US012250976B2

(12) United States Patent
Elbaz et al.

(10) Patent No.: US 12,250,976 B2
(45) Date of Patent: Mar. 18, 2025

(54) NURSING BRA

(71) Applicant: IKAR (ISRAEL) LTD, Raanana (IL)

(72) Inventors: Sivan Elbaz, Ra'anana (IL); Amit Ron Ronkin, Ramot HaShavim (IL); Roi Kurt Ballin, Hoboken, NJ (US); Noam Kenan Ben Natan, Kfar Saba (IL)

(73) Assignee: IKAR (ISRAEL) LTD, Kadima (IL)

( * ) Notice: Subject to any disclaimer, the term of this patent is extended or adjusted under 35 U.S.C. 154(b) by 52 days.

(21) Appl. No.: 18/030,359

(22) PCT Filed: Oct. 7, 2021

(86) PCT No.: PCT/IL2021/051209
§ 371 (c)(1),
(2) Date: Apr. 5, 2023

(87) PCT Pub. No.: WO2022/074658
PCT Pub. Date: Apr. 14, 2022

(65) Prior Publication Data
US 2023/0363467 A1    Nov. 16, 2023

(30) Foreign Application Priority Data
Oct. 8, 2020  (IL) .......................................... 277885

(51) Int. Cl.
*A41C 3/04*    (2006.01)
*A41C 3/00*    (2006.01)
(Continued)

(52) U.S. Cl.
CPC .............. *A41C 3/04* (2013.01); *A41C 3/0014* (2013.01); *A41C 3/0035* (2013.01); *A41C 3/144* (2013.01);
(Continued)

(58) Field of Classification Search
CPC ........ A41C 3/04; A41C 3/0014; A41C 3/0035
See application file for complete search history.

(56) References Cited

U.S. PATENT DOCUMENTS 6,074,272 A     6/2000 Hebert
7,448,936 B1 *  11/2008 Kemp-Dorsey ......... A41C 3/04
                                                450/36
(Continued)

FOREIGN PATENT DOCUMENTS

GB         2520235 A       5/2015
WO      2015142590 A1      9/2015
WO      2018234719 A1     12/2018

OTHER PUBLICATIONS

The 9 Best Nursing Bras of 2019; (Pampers.com) updated Oct. 15, 2019—https://www.pampers.com/en-us/best-babyproducts/feeding/best-nursing-bras.
(Continued)

*Primary Examiner* — Gloria M Hale
(74) *Attorney, Agent, or Firm* — CANTOR COLBURN LLP

(57) ABSTRACT

The present disclosure discloses a garment for being used as a nursing bra and a suitable breast pad that is adapted to be fitted into pad pockets of the nursing bra. The nursing bra is basically made of a seamless knitted fabric and with an attachment of additional second fabric layer to the seamless knitted fabric pad pockets are being formed between the seamless knitted fabric and the second fabric. These pad pockets are accessible from respective openings that are formed in the second fabric at a position suitable for receiving a nipple of a wearer such. Furthermore, the openings are designed so as to allow relatively easy insertion and removal of the breast pad into and from the pad pockets. Thus, when the breast pads are accommodated within the pad pockets, a nipple wearer engages the breast pads such (Continued)

that any leakage of breastmilk is absorbed by the breast pad and the rest of the bra maintains dry. The pads are secured in their position when being received in the pockets to avoid misalignment of the nipple with the pad such that even during activity or sleep, the pads maintain in contact with the nipple and absorb the liquid or moisture deriving therefrom.

20 Claims, 2 Drawing Sheets

(51) Int. Cl.
  *A41C 3/14* (2006.01)
  *A61F 13/14* (2006.01)
  *A61F 13/15* (2006.01)
  *A61F 13/84* (2006.01)
(52) U.S. Cl.
  CPC .. *A61F 13/141* (2013.01); *A61F 2013/15276* (2013.01); *A61F 2013/8414* (2013.01)

(56) References Cited

U.S. PATENT DOCUMENTS

| 2007/0015438 | A1 | 1/2007 | Lange | |
|---|---|---|---|---|
| 2012/0129427 | A1 | 5/2012 | Perez | |
| 2016/0021940 | A1* | 1/2016 | Carney | A41B 9/06 450/92 |
| 2018/0070653 | A1* | 3/2018 | Montford | A41C 3/0014 |

OTHER PUBLICATIONS

Infinity-Nursing-Breastfeeding-Polyester-Baby; (Amazon.ca) Date First Available Jun. 7, 2019 Retrieved from the Internet: https://www.amazon.ca/Infinity-Nursing-Breastfeeding-Polyester-Baby/dp/B07LC63258.

International Search Report for corresponding application PCT/IL2021/051209 filed Oct. 7, 2021; Mail date Dec. 30, 2021.

Yip, J. "Advanced textiles for intimate apparel." Advances in Women's Intimate Apparel Technology. Woodhead Publishing, Mar. 23, 2016.

Written Opinion for corresponding application PCT/IL2021/051209 filed Oct. 7, 2021; Mail date Dec. 30, 2021.

* cited by examiner

NURSING BRA

TECHNOLOGICAL FIELD

The present disclosure is in the field of nursing garments.

BACKGROUND ART

References considered to be relevant as background to the presently disclosed subject matter are listed below:
WO 2015/142590

Acknowledgement of the above references herein is not to be inferred as meaning that these are in any way relevant to the patentability of the presently disclosed subject matter.

BACKGROUND

Women who Breastfeeding are dealing with a constant leakage of breastmilk that moistening the bra. To avoid moistening of the bra, women are often use disposable pads that adhere to an inner portion of the bra to absorb the milk. This requires constantly maintaining the disposable pads in the right position and at time taking an unnecessary attention.

GENERAL DESCRIPTION

The present disclosure discloses a garment for being used as a nursing bra and a suitable breast pad that is adapted to be fitted into pad pockets of the nursing bra. The nursing bra is basically made of a seamless knitted fabric and with an attachment of additional second fabric layer to the seamless knitted fabric pad pockets are being formed between the seamless knitted fabric and the second fabric. These pad pockets are accessible from respective openings that are formed in the second fabric at a position suitable for receiving a nipple of a wearer such. Furthermore, the openings are designed so as to allow relatively easy insertion and removal of the breast pad into and from the pad pockets. Thus, when the breast pads are accommodated within the pad pockets, a nipple wearer engages the breast pads such that any leakage of breastmilk is absorbed by the breast pad and the rest of the bra maintains dry. The pads are secured in their position when being received in the pockets to avoid misalignment of the nipple with the pad such that even during activity or sleep, the pads maintain in contact with the nipple and absorb the liquid or moisture deriving therefrom.

The breast pads are uniquely designed for the nursing bra—they are formed of multiple layers, each serves for a different function; and are molded to obtain the cup shape. The pads are typically formed of four different layers and are arranged in the following order from the layer proximal to the nipple's wearer to the most distal layer from the nipple: (1) fast wicking mesh layer; (2) anti-microbial absorbent layer; (3) liquid-proof layer; (4) a single jersey layer.

Thus, an aspect of the present disclosure provides a garment, i.e. a nursing bra, that has a garment front and a garment back. Two breast cup portions defined in the garment front, and a bottom support portion positioned below the breast cup portion for tight fitting over a wearer's chest or belly. The garment is formed of:

(i) a single layer knitted seamless first fabric having an outer surface and an inner surface. Respective portions of the outer and inner surfaces of the single layer knitted seamless fabric define the breast cup portions.

(ii) at least one fabric sheet attached or seamed to the inner surface of said knitted seamless first fabric to define respective pad pockets for each breast cup portion between said at least one second fabric sheet and the inner surface of the breast cup portions. Namely, by attaching the second fabric to the first fabric a space is formed between them, this space constitutes the pockets. The at least one second fabric sheet comprises respective openings formed at central portions of said pad pockets for allowing (a) introduction and removal of breast pads into said pad pockets, and (b) receiving a nipple of the wearer such that it engages the interior of the pad pockets, and practically engaging the pad when it is inserted into the pad pockets).

It is to be noted that any combination of the described embodiments with respect to any aspect of this present disclosure is applicable. In other words, any aspect of the present disclosure can be defined by any combination of the described embodiments.

In some embodiments of the garment, the at least one second fabric sheet is a single fabric sheet, namely a single sheet that extends over the two cup portions.

In some embodiments of the garment, the at least one second fabric sheet is attached or seamed to the bottom support portion and to portions of the top end of the breast cup portions. It is to be noted that the ends may be defined along a profile of the edge of the cup portions and one portion of the top end may be lower than other portion.

In some embodiments of the garment, the second fabric is wrap knitted fabric.

In some embodiments of the garment, the breast cup portions are formed of a first fabric texture having a first elastic property. The breast support portions surrounding said breast cup portions are formed of a second fabric texture having a second elastic property. Namely, the first texture of the breast cup portions is typically less dense and/or more elastic than the breast support portions surrounding the breast cup portion having a texture denser and/or more elastic than the texture of the breast cup portion. It is to be noted that both portions are part of a single fabric, only having different textures that affect their elasticity, support degree and/or other fabric properties. Furthermore, it is to be noted that the breast support portions may be formed with several types of textures, each of them is denser and/or less elastic than the texture of the breast cup portions.

In some embodiments of the garment, the second fabric texture is denser than the first fabric texture and therefore is less elastic providing support to the breast of the wearer.

In some embodiments of the garment, the breast support portions are located in one or more of: (i) between the bottom support portion and the breast cup portions, (ii) between the breast cup portions and/or (iii) laterally peripheral to the breast portions towards the direction of the horizontal chest straps portion or the fasteners.

In some embodiments of the garment, the support portions are continuously linked to one another, namely they all linked to form a continuous supporting fabric texture surrounding the breast cup portions.

In some embodiments, the garment includes fasteners couple formed at opposite lateral sides of the garment and configured to be fastened one to another for fastening the garment around the wearer's chest and/or back. The fasteners may be, for example, hook and eye fasteners.

In some embodiments, the garment includes two sheets of a third fabric. Each of the sheets of the third fabric is attached, e.g. seamed, bonded or knitted to at least a respective bottom end of a breast cup portion and is couplable to the top end of the breast cup portion of the first fabric via a clipping arrangement. The clipping arrangement includes two clipping members, one is formed at a portion of the third fabric and one is formed at the top end of the breast cup portion. The third fabric serves for providing additional support to the breast of the wearer. Typically, the sheets of the third fabric are configured to support the side portions of the breast, thus they are attached at the peripheral portion of each cup portion.

In some embodiments of the garment, the third fabric is further attached to portions of the second fabric. For example, the third fabric may be seamed to the second fabric with a seam that extends between portions of the second fabric overlapping with the bottom end of the cup portion and top end of the cup portion.

In some embodiments of the garment, each of the third fabric sheets is seamed to the bottom end of the respective cup portion and is attachable to the top end of the breast cup portions.

In some embodiments of the garment, the third fabric is attached to one end of the shoulder strap and the second end of the shoulder strap is attached to the first fabric, e.g. seamed, or clipped thereto.

In some embodiments of the garment, each of the third fabric sheets extends over a portion of the respective opening. Namely, when the garment is not worn, each of the third fabric sheets covers a portion of the respective opening of the respective cup portion, when the third fabric is attached, e.g. clipped to the top end of the breast cup portion of the first fabric.

In some embodiments, the garment further includes the breast pads that are intended to be fitted into the pad pockets.

In some embodiments, the garment further includes shoulder straps extending at a top end of the garment between the garment front and the garment back for fitting over shoulders of a wearer. The shoulder straps are attached to the first fabric at one portion thereof and to the third fabric at a second portion thereof. The attachment can be by seams, via a clip in an attachable/detachable manner, or in any other suitable means. The shoulder straps can be also integral with one or both of the first and third fabric.

In some embodiments of the garment, at least two of the first, second and third fabrics are the same fabric. In other embodiment, each of the first, second and third fabrics are made of different types of fabrics.

In some embodiments of the garment, the breast pads are reusable, namely they are non-disposable pads that are washable for reusing them repeatedly.

Yet another aspect of the present disclosure provides a multi-layer reusable breast pad for fitting in a breast pad pocket. The breast pad includes (i) a nipple-engaging layer that is made of a knitted meshed fabric being a fast wicking mesh; (ii) a jersey fabric layer, being one of the outer layers, opposite to the nipple-engaging layer, and facing away from the body when being received in the breast pad pocket; (iii) an anti-microbial absorbent layer; and (iv) leak-proof layer or film. The anti-microbial absorbent layer is formed between the nipple-engaging layer and the leak-proof layer and the leak-proof layer is formed between the anti-microbial absorbent layer and the jersey fabric layer. Thus, the layers are arranged, from the nipple side to the external side as follows: (1) nipple-engaging layer; (2) anti-microbial absorbent layer; (3); leak-proof layer; and (4) jersey fabric layer). The breast pad is being molded, thereby having a cup shape.

In some embodiments of the breast pad, the nipple-engaging layer is made of or comprises polyester.

In some embodiments of the breast pad, the anti-microbial absorbent layer comprises polyester and/or anti-microbial agent.

In some embodiments, the anti-microbial absorbent layer comprises linolenic acid. The linolenic acid may have molecular bonding structure with the polyester.

In some embodiments of the breast pad, the anti-microbial agent is be selected from any one silver, copper, organosilanes, bactericides, viral inhibitors, fungal inhibitors, or any combination thereof.

In some embodiments of the breast pad, the leak-proof layer is made of or comprises polyester. The leak-proof layer is sufficiently dense such that liquid, such as breastmilk, does not penetrate therethrough and reaches the jersey layer.

In some embodiments of the breast pad, the jersey fabric layer is made of a single jersey.

In some embodiments of the breast pad, jersey fabric layer is made of or comprises polyester.

In some embodiments of the breast pad, the anti-microbial layer and the leak-proof layer are laminated one to another.

In some embodiments of the breast pad, the anti-microbial absorbent layer comprises 120-180 Denier (D) polyester and optionally copper. Preferably, the anti-microbial absorbent layer comprises about 150 D.

It is to be noted that the term "about" defines a range of ±20% from the value it describes. For example, about 150 D defines a range of ±15 D from 150 D, namely 135-165 D.

The breast pad of any one of the above embodiments may be used to be fitted in a pad pocket of the garment according to any one of the above embodiments.

Yet another aspect of the present disclosure provides a kit comprising the garment of any one of the above described embodiments and one or more breast pads of any one of the above described embodiments.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A shows the inner side of the garment and FIG. 1B shows the outer side of the garment.

DETAILED DESCRIPTION OF EMBODIMENTS

The following figures are provided to exemplify embodiments and realization of the invention of the present disclosure.

Figure 1A:
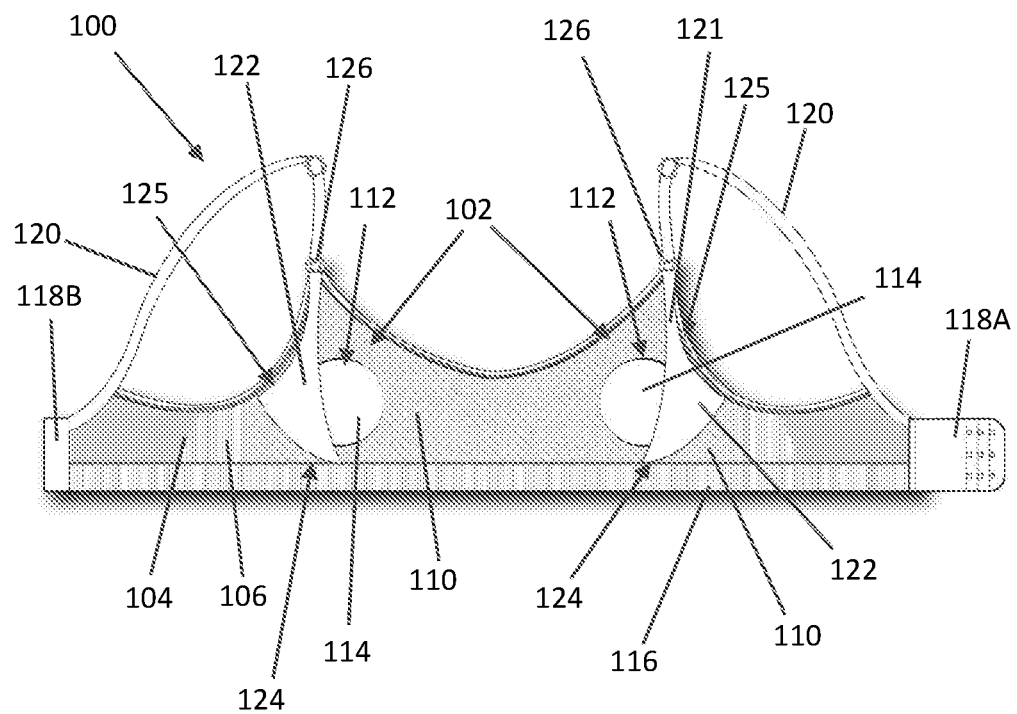
FIGS. 1A-1B are schematic illustrations of a non-limiting example of an embodiment of a garment according to an aspect of the present disclosure.
Figure 1B:
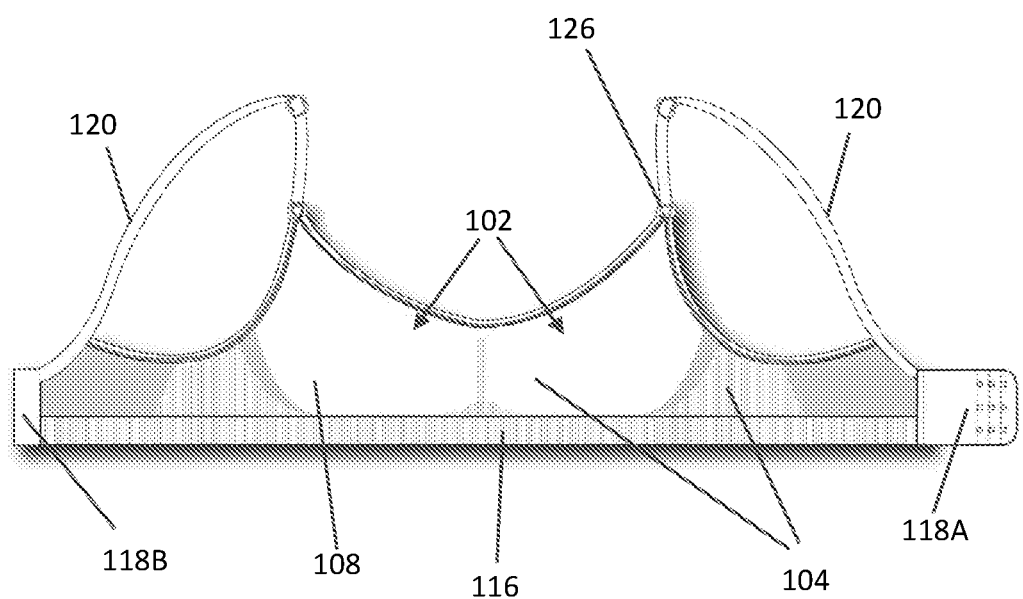

Reference is made to FIGS. 1A-1B, which are illustrations of inner and outer sides, respectively, of a non-limiting example of an embodiment of a garment serving as a nursing bra, according to an aspect of the present disclosure. The nursing bra 100 includes two breast cup portions 102 that are defined in the front of the nursing bra. The nursing bra 100 is formed of a single layer, knitted seamless first fabric 104 that is having an inner surface 106 and an outer surface 108.

The cup portions 102 are defined by respective portions of the inner and outer surfaces of the first fabric 104. A second fabric layer 110 is attached, e.g. knitted, seamed, or bonded to the inner surface 106 of the first fabric 104. The second fabric layer 110 is attached such that it overlaps with at least a portion of the inner surface of the portions defining the cup portions 102, thereby forming pad pockets 112 between the first fabric layer 104 and the second fabric layer 110. Two openings 114 are formed at the second fabric layer 110 at a suitable position to receive the nipples of the wearer, when the bra is worn. The pad pockets 112 are configured to accommodate nursing pads (not shown), which are insertable and removable through the openings 114. The openings 114 are shaped and dimensioned to facilitate said insertion and removal of the pads, for example the openings can be circular. The pads are reusable and can be washed with or separately from the bra.

The nursing bra 100 includes a bottom support portion 116 for tight fitting over a wearer's chest or belly and fasteners couple 118A and 118B at two opposite ends of the bottom support portion 116 to allow fastening of the bra around the wearer's chest or belly. The fasteners can be, for example, hook and eye closure.

The nursing bra 100 further includes adjustable shoulder straps 120 linking the front side and the back side of the bra for fitting over shoulders of a wearer.

Two sheets of a third fabric 122 are attached to the inner side of the cup portions 102 to provide additional support to the breast of the wearer. Each of the third fabrics 122 is attached to the bottom end portion 124 of the cup portion 102 and the second fabric 110. For example, the attachment to the second fabric may be seams extending between portions overlapping with the bottom and top end of the cup portion. The third fabric includes a loose portion 121 that is attachable in an attachable/detachable manner to the to a shoulder strap clip 126 at the top end portion 124 of the cup portion 102. In some configurations, it can also be attached to the bottom support portion 116.

The first, second and third fabrics can be three different fabrics or at least two of them can be the same fabric. The first, second and third fabric may differ from one another by texture of the fabric, i.e. one can have more or less dense fabric than the others or at least portions thereof that have different textures. In some other embodiments, at least two of the first, second and third fabrics are made of the same type of fabric, though each may include different textures of the fabric. The type of textures affects the elasticity and/or density of the fabric. For example, the textures may be selected from rib knit type, pique, jersey, weft knits such as single knits and double knits, etc.

The first fabric layer 104 of the bra 100 is formed with different texture portions, i.e. portions with different density of the fabric that yields different properties of the fabric, e.g. different elasticity of different portions. In this example, the portions surrounding the cup portions 102 are denser than the cup portions to provide support to the breast. Similarly, the bottom support portion 116 is denser than the cup portions 102.

Figure 2:
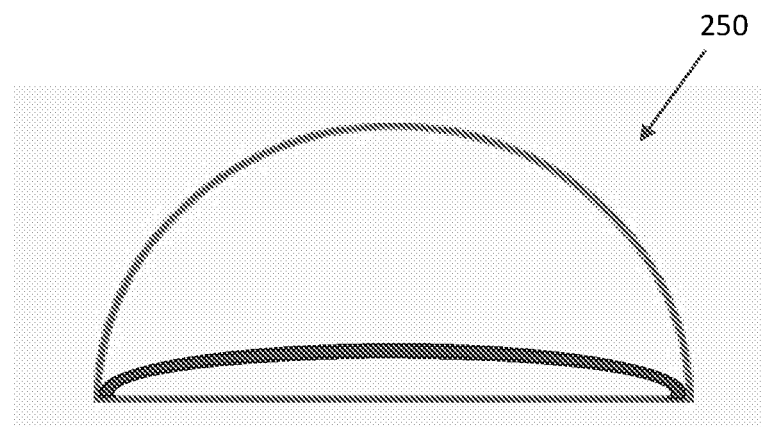
FIG. 2 is a schematic illustration of a side view of a non-limiting example of a breast pad according to an aspect of the present disclosure.

Reference is now made to FIG. 2, which is a side view of a schematic illustration of a non-limiting example of a nursing pad according to an aspect of the present disclosure. The nursing pad 250 is formed of multiple layers and the arrangement thereof is exemplified in FIG. 3. The nursing pad 250 is molded and thereby having a cup shape to be fitted into the pad pockets of the bra shown in FIG. 1A-1B.

Figure 3:
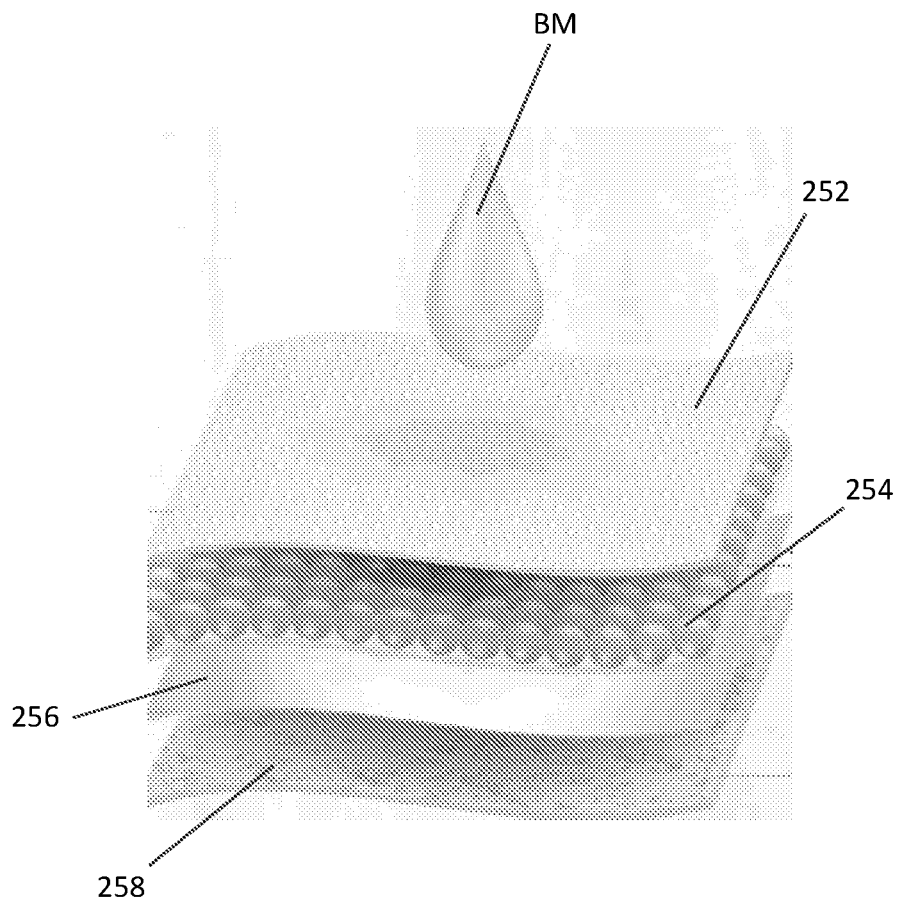
FIG. 3 is an illustration exemplifying an embodiment of the layer arrangement of the breast pad according to an aspect of the present disclosure.

Referring now to FIG. 3, the top layer is the nipple-engaging layer 252 that comes into contact with the nipple of the wearer when the pad is received in the pad pocked of the bra. The nipple-engaging layer 252 is made of a fast wicking mesh and breastmilk BM from the nipple is drained into the pad, namely to layers beyond the nipple-engaging layer 252. The layer adjacent to the nipple-engaging layer 252 is an anti-microbial absorbent layer 254 that has anti-microbial properties. The anti-microbial absorbent layer 254 is laminated to a leak-proof film 256 that is configured to block liquids penetration therethrough. The anti-microbial absorbent layer 254 is sandwiched between the nipple-engaging layer 252 and the leak-proof film 256. A single jersey layer 258 is adjacent to the leak-proof film from the opposite side of the leak-proof film such that the leak-proof film is sandwiched between the anti-microbial absorbent layer 254 and the single jersey layer 258. The leak-proof film blocks the flow of the liquids from the anti-microbial absorbent layer 254 side towards the single jersey layer 258, thereby the single jersey layer maintains dry and free of breastmilk. This is important since the single jersey layer 258 engages the cup portion and in case it is being moistened, the moisture passes to the cup portion and stains the bra and/or the garment that covers the bra, e.g. a shirt or a dress.

The invention claimed is:

1. A garment comprising:
   a garment front and a garment back, two breast cup portions defined in the garment front, and a bottom support portion positioned below the breast cup portion for tight fitting over a wearer's chest or belly;
   the garment being formed of
   (i) a single layer, knitted seamless first fabric having an outer and an inner surface, respective portions of the outer and inner surfaces thereof defining the breast cup portions, and
   (ii) a single second fabric sheet attached or seamed to the inner surface of said knitted seamless first fabric to define respective pad pockets for each breast cup portion between said second fabric sheet and the inner surface of the breast cup portions, the second fabric sheet comprises respective openings formed at central portions of said pad pockets for allowing (a) introduction and removal of breast pads into said pad pockets, and (b) receiving a nipple of the wearer such that it engages an interior of the pad pockets.

2. The garment of claim 1, wherein second fabric sheet is attached or seamed to the bottom support portion and a top end of the breast cup portions.

3. The garment of claim 1, wherein the second fabric is a warp knitted fabric.

4. The garment of claim 1, comprising shoulder straps extending at a top end of the garment between the garment front and the garment back for fitting over shoulders of a wearer being integral with the first fabric, or being made of a shoulder-strap fabric being the same or of a different than the first fabric and bonded to the first fabric.

5. The garment of claim 1, wherein the breast cup portions are formed of a first fabric texture having a first elastic property and breast support portions surrounding said breast cup portions are formed of a second fabric texture having a second elastic property.

6. The garment of claim 5, wherein the second fabric texture is denser than the first fabric texture.

7. The garment of claim 5, wherein the breast support portions are located between the bottom support portion and the breast cup portions, between the breast cup portions and laterally peripheral to the breast portions.

8. The garment of claim 7, wherein the support portions are continuous.

9. The garment of claim 1, comprising fasteners couple formed at opposite lateral sides of the garment and configured to be fastened one to another for fastening the garment around the wearer's chest and/or back; and further comprising two sheets of a third fabric, each attached to the bottom end of the breast cup portion and to a shoulder strap for providing additional support to the breast of the wearer.

10. The garment of claim 9, wherein each of the third fabric sheets is seamed to (i) the bottom end of the respective cup portion, (ii) a portion of the second fabric, and (iii) is attachable to the top end of the breast cup via a shoulder strap clip that is configured for clipping to the shoulder strap.

11. The garment of claim 10, wherein when the third fabric is attached to the top end of the breast cup portion, it extends over a portion of the respective opening.

12. The garment of claim 1, comprising said breast pads.

13. The garment of claim 1, comprising a multi-layer reusable breast pad fitted in said breast pad pockets, said breast pad comprises:

a nipple-engaging layer that is made of a knitted meshed fabric;

a jersey fabric layer;

an anti-microbial absorbent layer;

leak-proof layer;

the anti-microbial absorbent layer is formed between the nipple-engaging layer and the leak-proof layer and the leak-proof layer is formed between the anti-microbial absorbent layer and the jersey fabric layer;

wherein the breast pad is molded, thereby having a cup shape.

14. The garment of claim 13, wherein the nipple-engaging layer is made of polyester.

15. The garment of claim 13, wherein the anti-microbial absorbent layer comprises polyester and anti-microbial agents.

16. The garment of claim 13, wherein the leak-proof layer is made of polyester.

17. The garment of claim 13, wherein the jersey fabric layer is made of a single jersey.

18. The garment of claim 13, wherein the jersey fabric layer is made of polyester.

19. The garment of claim 13, wherein the anti-microbial layer and the leak-proof layer are laminated one to another;

wherein the anti-microbial absorbent layer comprises about 150 Denier (D) polyester; and wherein the anti-microbial absorbent layer comprises linolenic acid.

20. A garment comprising:

a garment front and a garment back, two breast cup portions defined in the garment front, and a bottom support portion positioned below the breast cup portion for tight fitting over a wearer's chest or belly;

the garment being formed of
(i) a single layer, knitted seamless first fabric having an outer and an inner surface, respective portions of the outer and inner surfaces thereof defining the breast cup portions, and
(ii) at least one fabric sheet attached or seamed to the inner surface of said knitted seamless first fabric to define respective pad pockets for each breast cup portion between said at least one second fabric sheet and the inner surface of the breast cup portions, the at least one second fabric sheet comprises respective openings formed at central portions of said pad pockets for allowing (a) introduction and removal of breast pads into said pad pockets, and (b) receiving a nipple of the wearer such that it engages an interior of the pad pockets.

* * * * *